United States Patent
Iserloh et al.

(10) Patent No.: US 7,812,013 B2
(45) Date of Patent: Oct. 12, 2010

(54) MACROCYCLIC HETEROCYCLIC ASPARTYL PROTEASE INHIBITORS

(75) Inventors: Ulrich Iserloh, Hoboken, NJ (US); Zhaoning Zhu, Plainsboro, NJ (US); Andrew Stamford, Chatham Township, NJ (US); Johannes H. Voigt, Cranford, NJ (US)

(73) Assignee: Schering Corporation, Kenilworth, NJ (US)

( * ) Notice: Subject to any disclaimer, the term of this patent is extended or adjusted under 35 U.S.C. 154(b) by 652 days.

(21) Appl. No.: 11/451,064

(22) Filed: Jun. 12, 2006

(65) Prior Publication Data

US 2006/0281729 A1 Dec. 14, 2006

Related U.S. Application Data

(60) Provisional application No. 60/690,542, filed on Jun. 14, 2005.

(51) Int. Cl.
*A01N 43/00* (2006.01)
*A61K 31/33* (2006.01)
*C07D 498/00* (2006.01)

(52) U.S. Cl. ................. 514/183; 540/456

(58) Field of Classification Search ............. None
See application file for complete search history.

(56) References Cited

U.S. PATENT DOCUMENTS

| | | | |
|---|---|---|---|
| 3,197,476 A | 7/1965 | Erner | |
| 3,200,123 A | 8/1965 | Richardson et al. | |
| 5,883,096 A | 3/1999 | Lowe et al. | |
| 5,889,006 A | 3/1999 | Lowe et al. | |
| 5,935,958 A | 8/1999 | Kozlowski et al. | |
| 5,952,349 A | 9/1999 | Asberom et al. | |
| 5,977,138 A | 11/1999 | Wang et al. | |
| 6,037,352 A | 3/2000 | Lowe et al. | |
| 6,043,255 A | 3/2000 | Lowe et al. | |
| 6,066,636 A | 5/2000 | Kozlowski et al. | |
| 6,294,554 B1 | 9/2001 | Clader et al. | |
| 6,458,812 B1 | 10/2002 | McKittrick et al. | |
| 2003/0004353 A1 | 1/2003 | Yasuda et al. | |
| 2006/0281729 A1 | 12/2006 | Iserloh et al. | |
| 2007/0072852 A1 | 3/2007 | Zhu et al. | |

FOREIGN PATENT DOCUMENTS

| | | |
|---|---|---|
| EP | 0 682 025 | 11/1995 |
| FR | 2 741 072 | 5/1997 |
| FR | 2 747 678 | 10/1997 |
| WO | WO 90/15058 | 12/1990 |
| WO | WO 01/16136 | 3/2001 |
| WO | WO 02/074719 | 9/2002 |
| WO | WO 03/031412 | 4/2003 |
| WO | WO 2005/003106 | 1/2005 |
| WO | WO 2005/058311 | 6/2005 |
| WO | WO 2006/116412 | 11/2006 |
| WO | WO 2007/092839 | 8/2007 |

OTHER PUBLICATIONS

Vippagunta et al. Advanced Drug Delivery Reviews, 2001, 48, 3-26.*
Balaban, Teodor Silviu, et al., "2-Aminopyrimidine Directed Self-Assembly of Zinc Porphyrins Containing Bulky 3,5-Di-tert-butylphenyl Groups", Journal of the American Chemical Society (2003), 125(14), 4233-4239; 2003:215204 (Abstract).
Brown, George Barremore, "Atelopidtoxin. Purification and Chemistry", University Microfilms, Ann Arbor, Order No. 73-4474 (1972) 186 pp.; 1973:401115 (Abstract).
Brownlee, T.C., et al., "Infrared absorption of substituents in heterocyclic systems. X. Amine-imine tautomerism by infrared spectroscopy: Further examples", Journal of the Chemical Society [Section] B: Physical Organic (1966), (8), 726-7; 1966:465084 (Abstract).
Coppola, Gary M., "Novel heterocycles. I. Synthesis and reactions of 6,7-dihydro-1H, 3H,5H-pyrido[3,2,1-ij][3,1]benzoxazine-1,3-dione", Journal of Heterocyclic Chemistry (1978), 15 (4), 645-7; 1979:22931 (Abstract).
Drusvyatskaya, S.K., et al., "Synthesis and anthelmintic properties of pyrimidinoperimidines", Khimiko-Farmatsevticheskii Zhurnal (1983), 17(2), 158-60; 1983:198150 (English Abstract).
Fuhrman, Frederick A., et al., "Toxin from skin of frogs of the genus *Atelopus*; differentiation from dendrobatid toxins", Science (Washington, DC, United States) (1969), 165(3900), 1376-7; 1969:521925 (Abstract).

(Continued)

*Primary Examiner*—James O Wilson
*Assistant Examiner*—Noble Jarrell
(74) *Attorney, Agent, or Firm*—Keith D. MacMillan; William Y. Lee

(57) ABSTRACT

Disclosed are compounds of the formula I

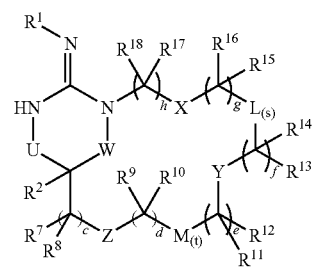

or a stereoisomer, tautomer, or pharmaceutically acceptable salt, solvate or ester thereof, wherein U, W, X, L, Y, M, Z, c, d, e, f, g, h, s, t, $R^1$, $R^2$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are as defined in the specification; and pharmaceutical compositions comprising the compounds of formula I.

Also disclosed is the method of inhibiting aspartyl protease, and in particular, the methods of treating cardiovascular diseases, cognitive and neurodegenerative diseases. Also disclosed are methods of treating cognitive or neurodegenerative diseases using the compounds of formula I in combination with a cholinesterase inhibitor or a muscarinic $m_1$ agonist or $m_2$ antagonist.

12 Claims, No Drawings

OTHER PUBLICATIONS

Golubushina, G.M., et al., "Condensation of 2-amino-3,4,5,6-tetrahydroimidazo [4,5,1-ij]quinoline and 2-amino-2-pyrrline with β-diketones", Khimiya Geterotsiklicheskikh Soedinenii (1972), (3), 419-21; 1972:488425 (English Abstract).

Henderson, R., et al., "Binding of labeled saxitoxin to the sodium channels in nerve membranes", Journal of Physiology (Cambridge, United Kingdom) (1973), 235(3), 783-804; 1974:116904 (Abstract).

Huang, Minta, et al., "Accumulation of cyclic adenosine monophosphate in incubated slices of brain tissue. 2. Effects of depolarizing agents, membrane stabilizers, phosphodiesterase inhibitors, and adenosine analogs", Journal of Medicinal Chemistry (1972), 15(5), 462-6; 1972:443058 (Abstract).

Iwamoto, Osamu, et al., "Total synthesis of (−)-decarbamoyloxysaxitoxin", Angewandte Chemie, International Edition (2007), 46(45), 8625-8628; 2007:1398087 (Abstract).

Kim, Yong Hae, et al., "Potent Neurotoxins: Tetrodotoxin, Chiriquitoxin, and Zetekitoxin from *Atelopus* Frogs in Central America", Journal of Toxicology, Toxin Reviews (2003), 22(4), 521-532; 2003:985614 (Abstract).

Kukla, Michael J., et al., "Synthesis and anti-HIV-1 activity of 4,5,6,7-tetrahydro-5-methylimidazo[4,5,1-jk] [1,4]benzodiazepin-2(1H)-one (TIBO) derivatives", Journal of Medicinal Chemistry (1991), 34(11), 3187-97; 1991:632195 (Abstract).

Mari, Yotsu-Yamashita, et al., "The structure of zetekitoxin from the Panamanian frog *Atelopus zeteki*", Tennen Yuki Kagobutsu Toronkai Koen Yoshishu (2000), 42$^{nd}$, 415-420; 2001:101914 (English Abstract).

Mitsumi, Minoru, et al., "Three-dimensional H-bonded networks based on mono- and tetranuclear metal-pteridine complexes", Molecular Crystals and Liquid Crystals Science and Technology, Section A: Molecular Crystals and Liquid Crystals (1996), 276, 229-235; 1996:295932 (Abstract).

Nagamatsu, Kentaro, et al., "Reactions of 8-(triphenylphosphoimino)quinoline with aryl aldehydes and aryl isocyanates: formation of 2-aryl-4H-imidazo[4,5,1-1-ij]quinolines and related systems", Heterocycles (2006), 69, 167-178; 2007:16172 (Abstract).

Poludnenko, V.G., et al., "Derivatives of 5,6-dihydro-4H-imidazo[4,5,1-i,j]quinoline. I. Synthesis and reactions of 2-amino derivatives", Khimiya Geterotsiklicheskikh Soedinenii (1970), (10), 1410-13; 1971:53657 (English Abstract).

Pozharskii, A.F., et al., "Heterocyclic analogs of pleiadiene. 53. Properties of 1,9-trimethyleneperimidine", Khimiya Geterotsiklicheskikh Soedinenii (1981), (7), 980-2; 1981:603864 (English Abstract).

Price, Clayton, et al., "Macrochelation, cyclometallation and G-quartet formation: N3-and C8-bound PdII complexes of adenine and guanine", Chemistry—A European Journal (2001), 7(6), 1194-1201; 2001:240418 (Abstract).

Richardson, Alfred, Jr., "The synthesis and chemistry of certain 2-substituted 5,6-dihydroimidazo-,-oxazolo-, and—thiazolo[ij]quinolines", Journal of Organic Chemistry (1963), 28(10), 2581-7; 1963:462271 (Abstract).

Roseen, Jill S., et al., "Comparison of the effects of atelopidtoxin with those of tetrodotoxin, saxitoxin, and batrachotoxin on beating of cultured chick heart cells", Toxicon (1971), 9(4), 411-15; 1972:21760 (Abstract).

Shindelman, Jeffrey, et al., "Atelopidtoxin from the Panamanian frog, *Atelopus zeteki*", Toxicon (1969), 7(4), 315-19; 1970:98699 (Abstract).

Simonov, A.M., et al., "Amination of 5,6-dihydro-4H-imidazo[4,5,1-i,j]quinoline", Khimiya Geterotsiklicheskikh Soedinenii (1969), (3), 567; 1969:524323 (English Abstract).

Simonov, A.M., et al., "Derivatives of 5,6-dihydro-4H-imidazo[4,5,1-i,j]quinoline. III, Substitution reactions in a 5,6-dihydro-4H-imidazo[4,5,1-i-j]quinoline series", Khimiya Geterotsiklicheskikh Soedinenii (1972), (2), 242-6; 1972:140645 (English Abstract).

Vilar, Santiago, et al., "Probabilistic Neural Network Model for the In Silico Evaluation of Anti-HIV Activity and Mechanism of Action", Journal of Medicinal Chemistry (2006), 49(3), 1118-1124; 2006:44967 (Abstract).

Werbel, Leslie M., et al., "Synthesis of 5,6,-dihydro-8-methoxy-4H-imidazo[4,5,1,-ij] quinolines and some related ring systems", Journal of Heterocyclic Chemistry (1968), 5(3), 371-8; 1968:436031 (Abstract).

Berge, Stephen M., et al., "Pharmaceutical Salts", Journal of Pharmaceutical Sciences, 1977, pp. 1-19; vol. 66, Issue 1.

Byoung-Kuk, Na, et al., "Aspartic proteases of Plasmodium vivax are highly conserved in wild isolates", The Korean Journal of Parasitology, 2004, pp. 61-66, vol. 42, No. 2.

Gould, Philip L., "Salt selection for basic drugs", International Journal of Pharmaceutics, 1986, pp. 201-217, vol. 33.

Moloney, Gerard P., et al., "A Novel Series of 2,5-Substituted Tryptamine Derivatives as Vascular $5HT_{1B/1D}$ Receptor Antagonists", J. Med. Chem., 1997, pp. 2347-2362, vol. 40, No. 15.

Oparil, Suzanne, et al., "The Renin-Angiotensin System (Second of Two Parts)", The New England Journal of Medicine, 1974, pp. 446-457, vol. 291, No. 9.

Yasuda, Yoshiyuki, et aL, "Characterization of New Fluorogenic Substrates for the Rapid and Sensitive Assay of Cathespin E and Cathespin D", J. Biochem, 1999, pp. 1137-1143, vol. 125, No. 6.

Intellectual Search Report for PCT/US 2006/022701, mailed Nov. 22, 2006 (3 pages) for CN06361.

* cited by examiner

MACROCYCLIC HETEROCYCLIC ASPARTYL PROTEASE INHIBITORS

CROSS REFERENCE TO RELATED APPLICATIONS

This application claims the benefit of U.S. Provisional Application No. 60/690,542 filed on Jun. 14, 2005.

FIELD OF THE INVENTION

This invention relates to macrocyclic heterocyclic aspartyl protease inhibitors, pharmaceutical compositions comprising said compounds, their use in the treatment of cardiovascular diseases, cognitive and neurodegenerative diseases, and their use as inhibitors of the Human Immunodeficiency Virus, plasmepsins, cathepsin D and protozoal enzymes.

BACKGROUND

Human aspartic proteases of the A1 (pepsin-like) family are as follows: pepsin A and C, renin, BACE, BACE 2, Napsin A, cathepsin D in pathological conditions.

The role of renin-angiotensin system (RAS) in regulation of blood pressure and fluid electrolyte has been well established (Oparil, S, et al. N Engl J Med 1974; 291:381-401/446-57). The octapeptide Angiotensin-II, a potent vasoconstrictor and stimulator for release of adrenal aldosterone, was processed from the precursor decapeptide Angiotensin-I, which in turn is processed from angiotensinogen by the renin enzyme. Angiotensin-II is also found to play roles in vascular smooth muscle cell growth, inflammation, reactive oxygen species generation and thrombosis and influence atherogenesis and vascular damage. Clinically, the benefit of interruption of the generation of angiotensin-II through antagonism of conversion of angiotensin-I has been well known and there are a number of ACE inhibitor drugs on the market. The blockade of the earlier conversion of angiotensinogen to angiotensin-I, i.e. the inhibition of renin enzyme, is expected to have similar but not identical effects. Since renin is an aspartyl protease whose only natural substrate is angiotensinogen, it is believed that there would be less frequent adverse effect for controlling high blood pressure and related symptoms regulated by angiotensin-II through its inhibition.

Another protease, Cathepsin-D, is involved in lysosomal biogenesis and protein targeting, and may also be involved in antigen processing and presentation of peptide fragments. It has been linked to numerous diseases including, Alzheimer's, Disease, connective tissue disease, muscular dystrophy and breast cancer.

Alzheimer's Disease (AD) is a progressive neurodegenerative disease that is ultimately fatal. Disease progression is associated with gradual loss of cognitive function related to memory, reasoning, orientation and judgment. Behavioral changes including confusion, depression and aggression also manifest as the disease progresses. The cognitive and behavioral dysfunction is believed to result from altered neuronal function and neuronal loss in the hippocampus and cerebral cortex. The currently available AD treatments are palliative, and while they ameliorate the cognitive and behavioral disorders, they do not prevent disease progression. Therefore there is an unmet medical need for AD treatments that halt disease progression.

Pathological hallmarks of AD are the deposition of extracellular β-amyloid (Aβ) plaques and intracellular neurofibrillary tangles comprised of abnormally phosphorylated protein tau. Individuals with AD exhibit characteristic Aβ deposits, in brain regions known to be important for memory and cognition. It is believed that Aβ is the fundamental causative agent of neuronal cell loss and dysfunction which is associated with cognitive and behavioral decline. Amyloid plaques consist predominantly of Aβ peptides comprised of 40-42 amino acid residues, which are derived from processing of amyloid precursor protein (APP). APP is processed by multiple distinct protease activities. Aβ peptides result from the cleavage of APP by β-secretase at the position corresponding to the N-terminus of Aβ, and at the C-terminus by γ-secretase activity. APP is also cleaved by α-secretase activity resulting in the secreted, non-amyloidogenic fragment known as soluble APP.

An aspartyl protease known as BACE-1 has been identified as the β-secretase activity responsible for cleavage of APP at the position corresponding to the N-terminus of Aβ peptides.

Accumulated biochemical and genetic evidence supports a central role of Aβ in the etiology of AD. For example, Aβ has been shown to be toxic to neuronal cells in vitro and when injected into rodent brains. Furthermore inherited forms of early-onset AD are known in which well-defined mutations of APP or the presenilins are present. These mutations enhance the production of Aβ and are considered causative of AD.

Since Aβ peptides are formed as a result of β-secretase activity, inhibition of BACE-1 should inhibit formation of Aβ peptides. Thus inhibition of BACE-1 is a therapeutic approach to the treatment of AD and other cognitive and neurodegenerative diseases caused by Aβ plaque deposition.

Human immunodeficiency virus (HIV), is the causative agent of acquired immune deficiency syndrome (AIDS). It has been clinically demonstrated that compounds such as indinavir, ritonavir and saquinavir which are inhibitors of the HIV aspartyl protease result in lowering of viral load. As such, the compounds described herein would be expected to be useful for the treatment of AIDS. Traditionally, a major target for researchers has been HIV-1 protease, an aspartyl protease related to renin.

In addition, Human T-cell leukemia virus type I (HTLV-I) is a human retrovirus that has been clinically associated with adult T-cell leukemia and other chronic diseases. Like other retroviruses, HTLV-I requires an aspartyl protease to process viral precursor proteins, which produce mature virions. This makes the protease an attractive target for inhibitor design. (Moore, et al. Purification of HTLV-I Protease and Synthesis of Inhibitors for the treatment of HTLV-I Infection 55th Southeast Regional Meeting of the American Chemical Society, Atlanta, Ga., US Nov. 16-19, 2003 (2003), 1073. CODEN; 69EUCH Conference, AN 2004:137641 CAPLUS).

Plasmepsins are essential aspartyl protease enzymes of the malarial parasite. Compounds for the inhibition of aspartyl proteases plasmepsins, particularly I, II, IV and HAP, are in development for the treatment of malaria. (Freire, et al. WO 2002074719. Na Byoung-Kuk, et al., Aspartic proteases of *Plasmodium vivax* are highly conserved in wild isolates, Korean Journal of Parasitology (2004 June), 42(2) 61-6. Journal code: 9435800) Furthermore, compounds used to target aspartyl proteases plasmepsins (e.g. I, II, IV and HAP), have been used to kill malarial parasites, thus treating patients thus afflicted.

Compounds that act as aspartyl protease inhibitors are described, for example, in application U.S. Ser. No. 11/010, 772, filed on Dec. 13, 2004, herein incorporated by reference.

SUMMARY OF THE INVENTION

The present invention relates to compounds having the structural formula I

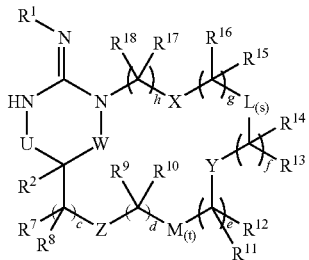

or a stereoisomer, tautomer, or pharmaceutically acceptable salt, solvate or ester thereof, wherein W is a bond, —C(=S)(C($R^3$)($R^4$))$_a$—, —(C($R^3$)($R^4$))$_a$C(=S)—, —S(O)$_{1-2}$(C($R^3$)($R^4$))$_a$—, —(C($R^3$)($R^4$))$_a$S(O)$_{1-2}$—, —C(=O)(C($R^3$)($R^4$))$_a$—, —(C($R^3$)($R^4$))$_a$C(=O)—, —O(C($R^3$)($R^4$))$_a$—, (C($R^3$)($R^4$))$_a$O—, —(C($R^3$)($R^4$))$_a$—, —N($R^5$)(C($R^3$)($R^4$))$_a$—, —(C($R^3$)($R^4$))$_a$N($R^5$)— or —C(=N($R^5$))(C($R^3$)($R^4$))$_a$—, —(C($R^3$)($R^4$))$_a$C(=N($R^5$))—; wherein a is 0-2;

U is a bond, —S(O)$_{1-2}$—, —C(=O)—, —O—, —P(O)(O$R^6$)—, —(C($R^3$)($R^4$))$_b$—, —N($R^5$)— or —C(=N($R^5$))—; wherein b is 0-2; provided that when W is —S(O)—, —S(O)$_2$—, —O—, or —N($R^5$)—, U is not —S(O)—, —S(O)$_2$—, —O—, or —N($R^5$)—;

$R^1$ and $R^5$ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, —O$R^{19}$, —CN, —C(O)$R^{20}$, —C(O)O$R^{19}$, —S(O)$_{1-2}R^{21}$, —C(O)N($R^{22}$)($R^{23}$), —S(O)$_{1-2}$N($R^{22}$)($R^{23}$), —NO$_2$, —N=C(R)($R^{23}$) and —N($R^{22}$)($R^{23}$); or $R^5$ is

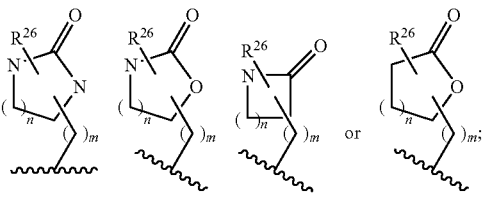

wherein $R^{26}$ numbers 0 to 5 substituents, m is 0 to 6 and n is 1 to 5;

$R^2$, $R^3$, $R^4$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, halo, —CF$_3$, —SH, —O$R^{19}$, —CN, —C(O)$R^{20}$, —C(O)O$R^{19}$, —S(O)$_{0-2}R^{21}$, —S(O)$_{1-2}$N($R^{22}$)($R^{23}$), —C(O)N($R^{22}$)($R^{23}$), —N($R^{22}$)C(O)$R^{20}$, —N($R^{22}$)C(O)N($R^{22}$)($R^{23}$), —N($R^{22}$)C(O)O$R^{19}$, —N($R^{22}$)S(O)$_{1-2}R^{21}$, —NO$_2$, —N=C($R^{22}$)($R^{23}$) and —N($R^{22}$)($R^{23}$); wherein c, d, e, f, g and h are 0-4;

X, Y and Z are independently selected from the group consisting of —O—, —N($R^5$)—, —C(O)—, —S(O)$_{0-2}$—, —C(O)N($R^{22}$)—, —N($R^{22}$)C(O)—, —S(O)$_{1-2}$N($R^{22}$)—, —N($R^{22}$)S(O)$_{1-2}$— or a bond;

L$_{(s)}$ and M$_{(t)}$ are independently selected from the group consisting of cycloalkylene, heterocycloalkylene, alkenylene, alkynylene, arylene, heteroarylene, or a bond; wherein the ring atoms of L and M are optionally substituted with 1 to 5 $R^{24}$ groups independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, halo, —CF$_3$, —SH, —O$R^{19}$, —CN, —C(O)$R^{20}$, —C(O)O$R^{19}$, —S(O)$_{0-2}R^{21}$, —S(O)$_{1-2}$N($R^{22}$)($R^{23}$), —C(O)N($R^{22}$)($R^{23}$), —N($R^{22}$)C(O)$R^{20}$, —N($R^{22}$)C(O)N($R^{22}$)($R^{23}$), —N($R^{22}$)C(O)O$R^{19}$, —N($R^{22}$)S(O)$_{1-2}R^{21}$, —NO$_2$, —N=C($R^{22}$)($R^{23}$) and —N($R^{22}$)($R^{23}$); wherein s is 1 or 2 and t is 1 or 2;

$R^{19}$ is H, alkyl, alkenyl, alkynyl, aryl, cycloalkyl, cycloalkylalkyl, heteroaryl, arylalkyl, heteroarylalkyl, heterocycloalkyl or heterocycloalkylalkyl;

$R^{20}$ is H, alkyl, alkenyl, alkynyl, aryl, cycloalkyl, cycloalkylalkyl, heteroaryl, arylalkyl, heteroarylalkyl, heterocycloalkyl, heterocycloalkylalkyl or —N($R^{23}$)($R^{24}$);

$R^{21}$ is alkyl, alkenyl, alkynyl, aryl, cycloalkyl, cycloalkylalkyl, heteroaryl, arylalkyl, heteroarylalkyl, heterocycloalkyl or heterocycloalkylalkyl;

$R^{22}$ and $R^{23}$ are H, alkyl, alkenyl, alkynyl, aryl, cycloalkyl, cycloalkylalkyl, heteroaryl, arylalkyl, heteroarylalkyl, heterocycloalkyl or heterocycloalkylalkyl;

provided that (i) when U is a bond, —O— or —N($R^5$)—, then $R^2$ is not selected from the group consisting of halo, —SH, —O$R^{19}$, —S(O)$_{0-2}R^{21}$, —S(O)$_{1-2}$N($R^{22}$)($R^{23}$), —N($R^{22}$)C(O)$R^{20}$, —N($R^{22}$)C(O)N($R^{22}$)($R^{23}$), —N($R^{22}$)C(O)O$R^{19}$, —N($R^{22}$)S(O)$_{1-2}R^{21}$, —NO$_2$, —N=C($R^{22}$)($R^{23}$) and —N($R^{22}$)($R^{23}$);

(ii) when W is —O(C($R^3$)($R^4$))$_a$— or —N($R^5$)(C($R^3$)($R^4$))$_a$— and a is 0, then $R^2$ is not selected from the group consisting of halo, —SH, —O$R^{19}$, —S(O)$_{0-2}R^{21}$, —S(O)$_{1-2}$N($R^{22}$)($R^{23}$), —N($R^{22}$)C(O)$R^{20}$, —N($R^{22}$)C(O)N($R^{22}$)($R^{23}$), —N($R^{22}$)C(O)O$R^{19}$, —N($R^{22}$)S(O)$_{1-2}R^{21}$, —NO$_2$, —N=C($R^{22}$)($R^{23}$) and —N($R^{22}$)($R^{23}$);

(iii) when W is —O(C($R^3$)($R^4$))$_a$— or —N($R^5$)(C($R^3$)($R^4$))$_a$— and a is 1 or 2, then $R^3$ and $R^4$ on the carbon atom adjacent to the heteroatom of W, are not selected from the group consisting of halo, —SH, —O$R^{19}$, —S(O)$_{0-2}R^{21}$, —S(O)$_{1-2}$N($R^{22}$)($R^{23}$), —N($R^{22}$)C(O)$R^{20}$, —N($R^{22}$)C(O)N($R^{22}$)($R^{23}$), —N($R^{22}$)C(O)O$R^{19}$, —N($R^{22}$)S(O)$_{1-2}R^{21}$, —NO$_2$, —N=C($R^{22}$)($R^{23}$) and —N($R^{22}$)($R^{23}$);

(iv) when U is a bond, —O— or —N($R^5$)— and c is 0, then Z is not —O—, —N($R^5$)—, —S(O)$_{0-2}$—, —N($R^{22}$)C(O)—, —S(O)$_{1-2}$N($R^{22}$)— or —N($R^{22}$)S(O)$_{1-2}$—;

(iv) when W is —O(C($R^3$)($R^4$))$_a$— or —N($R^5$)(C($R^3$)($R^4$))$_a$— and a and c are 0, then Z is not —O—, —N($R^5$)—, —S(O)$_{0-2}$—, —N($R^{22}$)C(O)—, —S(O)$_{1-2}$N($R^{22}$)— or —N($R^{22}$)S(O)$_{1-2}$—;

(v) when Z is —O— or —N($R^5$)—, then $R^7$, $R^8$, $R^9$ and $R^{10}$ on the carbon atom adjacent to Z are not selected from the group consisting of halo —SH, —O$R^{19}$, —S(O)$_{0-2}R^{21}$, —S(O)$_{1-2}$N($R^{22}$)($R^{23}$)—N($R^{22}$)C(O)$R^{20}$, —N($R^{22}$)C(O)N($R^{22}$)($R^{23}$), —N($R^{22}$)C(O)O$R^{19}$, —N($R^{22}$)S(O)$_{1-2}R^{21}$, —NO$_2$, —N=C($R^{22}$)($R^{23}$) and —N($R^{22}$)($R^{23}$);

(vi) when Y is —O— or —N($R^5$)—, then $R^{11}$, $R^{12}$, $R^{13}$ and $R^{14}$ on the carbon atom adjacent to Y are not selected from the group consisting of halo, —SH, —O$R^{19}$, —S(O)$_{0-2}R^{21}$, —S(O)$_{1-2}$N($R^{22}$)($R^{23}$), —N($R^{22}$)C(O)$R^{20}$, —N($R^{22}$)C(O)N($R^{22}$)($R^{23}$), —N($R^{22}$)C(O)O$R^{19}$, —N($R^{22}$)S(O)$_{1-2}R^{21}$, —NO$_2$, —N=C($R^{22}$)($R^{23}$) and —N($R^{22}$)($R^{23}$);

(vii) when X is —O— or —N($R^5$)—, then $R^{15}$, $R^{16}$, $R^{17}$ and $R^{18}$ on the carbon atom adjacent to X are not selected from the group consisting of halo, —SH, —$OR^{19}$, —S(O)$_{0-2}$$R^{21}$, —S(O)$_{1-2}$N($R^{22}$)($R^{23}$), —N($R^{22}$)C(O)$R^{20}$, —N($R^{22}$)C(O)N($R^{22}$)($R^{23}$), —N($R^{22}$)C(O)$OR^{19}$, —N($R^{22}$)S(O)$_{1-2}$$R^{21}$, —NO$_2$, —N=C($R^{22}$)($R^{23}$) and —N($R^{22}$)($R^{23}$);

(viii) when d and e are both zero and M is a bond, then Z or Y cannot both be —O—;

(ix) when f and g are both zero and L is a bond, then Y or X cannot both be —O—;

(x) when h is 1, then X is not —O— or —N($R^5$)—;

(xi) X, L, M, Y, Z and the carbon atoms of —(C($R^{17}$)($R^{18}$))$_h$—, —(C($R^{15}$)($R^{16}$))$_g$—, —(C($R^{13}$)($R^{14}$))$_f$—, —(C($R^{11}$)($R^{12}$))$_e$—, —(C($R^9$)($R^{10}$))$_d$— and —(C($R^7$)($R^8$))$_c$—, together with W, the carbon of —C($R^2$)— and the nitrogen atom to which W is attached form a ring of at least 5 atoms;

(xii) when W is a bond, then the ring formed by X, L, M, Y, Z and the carbon atoms of —(C($R^{17}$)($R^{18}$))$_h$—, —(C($R^{15}$)($R^{16}$))$_g$—, —(C($R^{13}$)($R^{14}$))$_f$—, —(C($R^{11}$)($R^{12}$))$_e$—, —(C($R^9$)($R^{10}$))$_d$—, —(C($R^7$)($R^8$))$_c$—, W, the carbon of —C($R^2$)— and the nitrogen atom attached to W, has a ring size greater than 9 atoms;

and wherein each of the alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl groups in the above definitions is independently unsubstituted or substituted by 1 to 5 $R^{26}$ moieties independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, arylcycloalkyl, halo, haloalkyl, haloalkoxy, —CN, —CF$_3$, —SH, —$OR^{19}$, —CN, —CH($R^{22}$)$R^{23}$), —C(O)$R^{20}$, —C(O)$OR^{19}$, —C(=NOR$^{19}$)$R^{22}$, —P(O)($OR^{19}$)($OR^{19}$), —S(O)$_{0-2}$$R^{21}$, —S(O)$_{1-2}$N($R^{22}$)($R^{23}$), —C(O)N($R^{22}$)($R^{23}$), —N($R^{22}$)C(O)$R^{20}$, -alkyl-N($R^{22}$)C(O)$R^{20}$, —N($R^{22}$)C(O)N($R^{22}$)($R^{23}$), -alkyl-N($R^{22}$)C(O)N($R^{22}$)($R^{23}$), —CH$_2$—$R^{22}$, —N($R^{22}$)C(O)$OR^{19}$, —N($R^{22}$)S(O)$_{1-2}$$R^{21}$, —N($R^{22}$)S(O)$_{1-2}$N($R^{22}$)($R^{23}$), —N$_3$, —NO$_2$, —N=C($R^{22}$)($R^{23}$), =NOR$^{19}$—N($R^{22}$)($R^{23}$) and -alkyl-N($R^{22}$)($R^{23}$);

wherein each of the alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, arylcycloalkyl, halo, haloalkyl and haloalkoxy in the above $R^{26}$ group is independently unsubstituted or substituted by 1 to 5 $R^{27}$ moieties independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, arylcycloalkyl, halo, haloalkyl, haloalkoxy, —CN, —CF$_3$, —SH, —$OR^{19}$, —CN, —CH($R^{22}$)$R^{23}$), —C(O)$R^{20}$, —C(O)$OR^{19}$, —C(=NOR$^{19}$)$R^{22}$, —P(O)($OR^{19}$)($OR^{19}$), —S(O)$_{0-2}$$R^{21}$, —S(O)$_{1-2}$N($R^{22}$)($R^{23}$), —C(O)N($R^{22}$)($R^{23}$), —N($R^{22}$)C(O)$R^{20}$, -alkyl-N($R^{22}$)C(O)$R^{20}$, —N($R^{22}$)C(O)N($R^{22}$)($R^{23}$), -alkyl-N($R^{22}$)C(O)N($R^{22}$)($R^{23}$), —CH$_2$—$R^{22}$, —N($R^{22}$)C(O)$OR^{19}$, —N($R^{22}$)S(O)$_{1-2}$$R^{21}$, —N($R^{22}$)S(O)$_{1-2}$ N($R^{22}$)($R^{23}$), —N$_3$, —NO$_2$, —N=C($R^{22}$)($R^{23}$), =NOR$^{19}$—N($R^{22}$)($R^{23}$) and -alkyl-N($R^{22}$)($R^{23}$).

In another aspect, the invention relates to a pharmaceutical composition comprising at least one compound of formula I and a pharmaceutically acceptable carrier.

In another aspect, the invention comprises the method of inhibiting aspartyl proteases comprising administering at least one compound of formula I to a patient in need of such treatment.

More specifically, the invention comprises: the method of treating a cardiovascular disease such as hypertension, renal failure, congestive heart failure or another disease modulated by renin inhibition; the method of treating Human Immunodeficiency Virus; the method of treating a cognitive or neurodegenerative disease such as Alzheimer's Disease; the method of inhibiting plasmepsins I and II for treatment of malaria; the method of inhibiting Cathepsin D for the treatment of Alzheimer's Disease, breast cancer, and ovarian cancer; and the method of inhibiting protozoal enzymes, for example inhibition of plasmodium falciparnum, for the treatment of fungal infections. Said method of treatment comprise administering at least one compound of formula I to a patient in need of such treatment. In particular, the invention comprises the method of treating Alzheimer's Disease comprising administering at least one compound of formula I to a patient in need of such treatment.

In another aspect, the invention comprises the method of treating Alzheimer's Disease comprising administering to a patient in need of such treatment a combination of at least one compound of formula I and a cholinesterase inhibitor or a muscarinic $m_1$ agonist or $m_2$ antagonist.

In a final aspect, the invention relates to a kit comprising in separate containers in a single package pharmaceutical compositions for use in combination, in which one-container comprises a compound of formula I in a pharmaceutically acceptable carrier and a second container comprises a cholinesterase inhibitor or a muscarinic $m_1$ agonist or $m_2$ antagonist in a pharmaceutically acceptable carrier, the combined quantities being an effective amount to treat a cognitive disease or neurodegenerative disease such as Alzheimer's Disease.

DETAILED DESCRIPTION

In general, it is understood that divalent groups, for example, but not necessarily limited to, —C(O)(C($R^3$)($R^4$))$_a$— are to be read left to right.

Preferred compounds of formula I are those compounds wherein W is —C(O)(C($R^3$)($R^4$))$_a$—.

Alternatively, another group of preferred compounds of formula I are those compounds wherein a is 0.

Another group of preferred compounds of formula I are those compounds wherein a is 1.

Another group of preferred compounds of formula I are those compounds wherein c, d, f and h are each 0.

More preferred compounds of the invention are those compounds of formula I, wherein e is 2-4.

More preferred compounds of the invention are those compounds of formula I, wherein g is 1.

More preferred compounds of the invention are those compounds of formula I, wherein X and Z are each a bond.

More preferred compounds of the invention are those compounds of formula I, wherein Y is —C(O)N($R^{22}$)— or —C(O)—.

Another group of preferred compounds of formula I are those compounds wherein Y is —C(O)— or —S(O)$_{1-2}$—.

Another group of preferred compounds of formula I are those compounds wherein L is a heterocycloalkylene group.

In yet another group of preferred compounds of formula I are those compounds wherein L and M are arylene or heteroarylene groups optionally substituted with 1 to 5 $R^{24}$ moieties.

Another group of preferred compounds of formula I are those compounds wherein M is an arylene or heteroarylene group optionally substituted with 1 to 5 $R^{24}$ moieties.

Another group of preferred compounds of formula I are those compounds wherein c is 1-2 or wherein d, f and h are 0.

In yet another group of preferred compounds of formula I are those compounds wherein L is an arylene or heteroarylene groups optionally substituted with 1 to 5 $R^{24}$ moieties.

In yet another group of preferred compounds of formula I are those compounds wherein L is a heterocycloalkylene group optionally substituted with 1 to 5 $R^{24}$ moieties.

In yet another group of preferred compounds of formula I are those compounds wherein M is an arylene or heteroarylene group optionally substituted with 1 to 3 $R^{24}$ moieties.

In yet another group of preferred compounds of formula I are those compounds wherein L is an arylene or heteroarylene groups optionally substituted with 1 to 5 $R^{24}$ moieties.

In yet another group of preferred compounds of formula I are those compounds wherein M is a heterocycloalkylene group optionally substituted with 1 to 5 $R^{24}$ moieties.

Compounds of formula I are those compounds wherein $R^2$ and $R^{24}$ are as defined above and U is a bond; W is —C(O)(C($R^3$)($R^4$))$_a$—; a is 0; c, d, f and h are 0; e is 2-4; g is 1; X and Z are each a bond; Y is —C(O)N($R^{22}$)— or —C(O)—; and L and M are arylene or heteroarylene groups optionally substituted with 1 to 5 $R^{24}$ moieties.

More preferred compounds of the invention are those compounds of formula I, wherein $R^2$ and $R^{24}$ are as defined above and U is a bond; W is —C(=O)(C($R^3$)($R^4$))$_a$—; a is 0; c, d, f and h are 0; e is 2-4; g is 1; X and Z are each a bond; Y is —C(O)— or —S(O)$_{1-2}$—; L is a heterocycloalkylene group, and M is an arylene or heteroarylene group optionally substituted with 1 to 5 $R^{24}$ moieties.

More preferred compounds of the invention are those compounds of formula 1, wherein M, $R^2$ and $R^{24}$ are as defined above and U is a bond; W is —C(=O)(C($R^3$)($R^4$))$_a$—; a is 0; d, f and h are 0; c is 1-2; e is 2-4; g is 1; X and Z are each a bond; Y is —C(O)N($R^{22}$)— or —C(O)—; and L is an arylene or heteroarylene groups optionally substituted with 1 to 5 $R^{24}$ moieties.

Another group of preferred compounds of formula I are those compounds wherein M, $R^2$ and $R^{24}$ are as defined above and U is a bond; W is —C(=O)(C($R^3$)($R^4$))$_a$—; a is 0; d, f and h are 0; c is 1-2; e is 2-4; g is 1; X and Z are each a bond; Y is —C(O)— or —S(O)$_{1-2}$—; and L is a heterocycloalkylene group optionally substituted with 1 to 5 $R^{24}$ moieties.

In yet another group of preferred compounds of formula I are those compounds wherein $R^2$ and $R^{24}$ are as defined above and U is a bond; W is —C(=O)(C($R^3$)($R^4$))$_a$—; a is 1; c, d, f and h are 0; e is 2-4; g is 1; X and Z are each a bond, Y is —C(O)N($R^{22}$)— or —C(O)—; and L and M are arylene or heteroarylene groups optionally substituted with 1 to 5 $R^{24}$ moieties.

In yet another group of preferred compounds of formula I are those compounds wherein $R^2$ and $R^{24}$ are as defined above and U is a bond, W is —C(=O)(C($R^3$)($R^4$))$_a$—, a is 1; c, d, f and h are 0; e is 2-4, g is 1; X and Z are each a bond, Y is —C(O)— or —S(O)$_{1-2}$—; and L is a heterocycloalkylene group, and M is an arylene or heteroarylene group optionally substituted with 1 to 3 $R^{24}$ moieties.

In another preferred embodiment are those compounds of formula I wherein M, $R^2$ and $R^{24}$ are as defined above, U is a bond; W is —C(=O)(C($R^3$)($R^4$))$_a$—; a is 1; d, f and h are 0; c is 1-2; e is 2-4; g is 1; X and Z are each a bond, Y is —C(O)N($R^{22}$)— or —C(O)—; and L is an arylene or heteroarylene groups optionally substituted with 1 to 5 $R^{24}$ moieties.

In yet another preferred embodiment are those compounds of formula I wherein M, $R^2$ and $R^{24}$ are as defined above, U is a bond; W is —C(=O)(C($R^3$)($R^4$))$_a$—; a is 1; d, f and h are 0; c is 1-2; e is 2-4; g is 1; X and Z are each a bond, Y is —C(O)— or —S(O)$_{1-2}$—; and L is a heterocycloalkylene group optionally substituted with 1 to 5 $R^{24}$ moieties.

It is noted that the carbons of formula I may be replaced with 1 to 3 silicon atoms so long as all valency requirements are satisfied.

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl, n-butyl, t-butyl, n-pentyl, heptyl, nonyl and decyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl.

"Aryl" means an aromatic monocyclic or multicyclic ring system comprising about 6 to about 14 carbon atoms, preferably about 6 to about 10 carbon atoms. The aryl group can be optionally substituted with one or more substituents (e.g., $R^{18}$, $R^{21}$, $R^{22}$, etc.) which may be the same or different, and are as defined herein or two substituents on adjacent carbons can be linked together to form

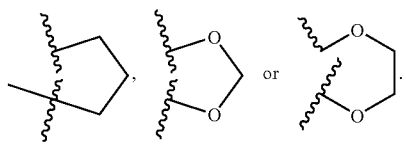

Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one to eight of the ring atoms is an element other than carbon, for example nitrogen, oxygen or sulfur, alone or in combination. Preferred heteroaryls contain about 5 to about 6 ring atoms. The "heteroaryl" can be optionally substituted by one or more $R^{21}$ substituents which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more substituents which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like. Further non-limiting examples of cycloalkyl include the following

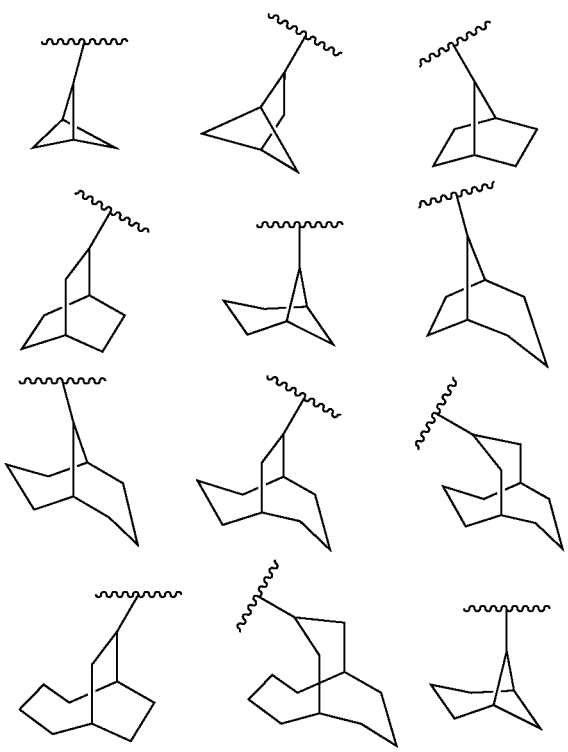

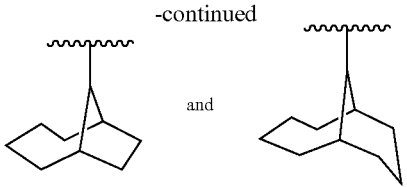

-continued and

"Cycloalkylether" means a non-aromatic ring of 3 to 7 atoms comprising an oxygen atom and 2 to 6 carbon atoms. Ring carbon atoms can be substituted, provided that substituents adjacent to the ring oxygen do not include halo or substituents joined to the ring through an oxygen, nitrogen or sulfur atom.

"Cycloalkenyl" means a non-aromatic mono or multicyclic ring system comprising about 3 to about 10 carbon atoms, preferably about 5 to about 10 carbon atoms which contains at least one carbon-carbon double bond. The cycloalkenyl ring can be optionally substituted with one or more $R^{21}$ substituents which may be the same or different, and are as defined above. Preferred cycloalkenyl rings contain about 5 to about 7 ring atoms. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" means a non-aromatic monocyclic or multicyclic ring system comprising about 3 to about 14 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more $R^{21}$ substituents which may be the same or different. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridyl, 1,2-dihydropyridyl, 1,4-dihydropyridyl, 1,2,3,6-tetrahydropyridyl, 1,4,5,6-tetrahydropyrimidyl, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Halo" means fluoro, chloro, bromo, or iodo groups. Preferred are fluoro, chloro or bromo, and more preferred are fluoro and chloro.

"Haloalkyl" means an alkyl as defined above wherein one or more hydrogen atoms on the alkyl is replaced by a halo group defined above.

"Heterocyclyl" (or heterocycloalkyl) means a non-aromatic saturated monocyclic or multicyclic ring system comprising about 3 to about 10 ring atoms, preferably about 5 to about 14 ring atoms, in which 1-3, preferably 1 or 2 of the atoms in the ring system is an element other than carbon, for example nitrogen, oxygen or sulfur, alone or in combination.

There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more $R^{21}$ substituents which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthamethyl. The bond to the parent moiety is through the alkyl.

"Arylcycloalkyl" means a group derived from a fused aryl and cycloalkyl as defined herein. Preferred arylcycloalkyls are those wherein aryl is phenyl and cycloalkyl consists of about 5 to about 6 ring atoms. The arylcycloalkyl can be optionally substituted by 1-5 $R^{21}$ substituents. Non-limiting examples of suitable arylcycloalkyls include indanyl and 1,2,3,4-tetrahydronaphthyl and the like. The bond to the parent moiety is through a non-aromatic carbon atom.

"Arylheterocycloalkyl" means a group derived from a fused aryl and heterocycloalkyl as defined herein. Preferred arylcycloalkyls are those wherein aryl is phenyl and heterocycloalkyl consists of about 5 to about 6 ring atoms. The arylheterocycloalkyl can be optionally substituted by 1-5 $R^{21}$ substituents. Non-limiting examples of suitable arylheterocycloalkyls include

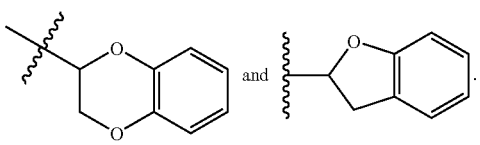

The bond to the parent moiety is through a non-aromatic carbon atom.

Similarly, "heteroarylalkyl" "cycloalkylalkyl" and "heterocycloalkylalkyl" mean a heteroaryl-, cycloalkyl- or heterocycloalkyl-alkyl-group in which the heteroaryl, cycloalkyl, heterocycloalkyl and alkyl are as previously described. Preferred groups contain a lower alkyl group. The bond to the parent moiety is through the alkyl.

"Acyl" means an H—C(O)—, alkyl-C(O)—, alkenyl-C(O)—, alkynyl-C(O)— or cycloalkyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Alkoxyalkyl" means a group derived from an alkoxy and alkyl as defined herein. The bond to the parent moiety is through the alkyl.

"Arylalkenyl" means a group derived from an aryl and alkenyl as defined herein. Preferred arylalkenyls are those wherein aryl is phenyl and the alkenyl consists of about 3 to about 6 atoms. The arylalkenyl can be optionally substituted by one or more $R^{27}$ substituents. The bond to the parent moiety is through a non-aromatic carbon atom.

"Arylalkynyl" means a group derived from a aryl and alkynyl as defined herein. Preferred arylalkynyls are those wherein aryl is phenyl and the alkynyl consists of about 3 to about 6 atoms. The arylalkynyl can be optionally substituted by one or more $R^{27}$ substituents. The bond to the parent moiety is through a non-aromatic carbon atom.

The suffix "ene" on alkyl, aryl, hetercycloalkyl, etc. indicates a divalent moiety, e.g., —CH$_2$CH$_2$— is ethylene, and

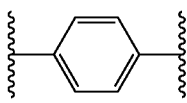

is para-phenylene.

It is understood that multicyclic divalent groups, for example, arylheterocycloalkylene, can be attached to other groups via bonds that are formed on either ring of said group. For example,

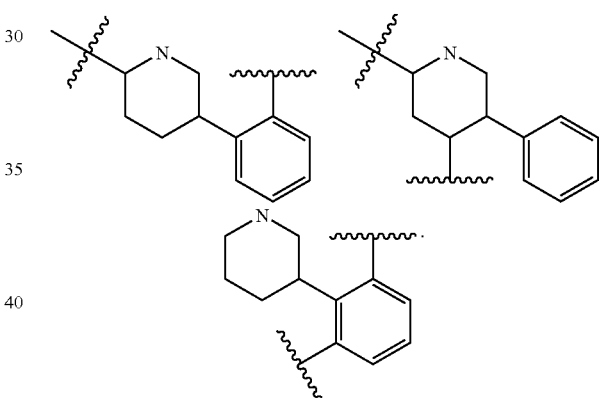

The term "optionally substituted" means optional substitution with the specified groups, radicals or moieties, in available position or positions.

Substitution on a cycloalkylalkyl, heterocycloalkylalkyl, arylalkyl, or heteroarylalkyl moiety includes substitution on the ring portion and/or on the alkyl portion of the group.

When a variable appears more than once in a group, or a variable appears more than once in the structure of formula I, e.g., $R^5$ may appear in both U and W, the variables can be the same or different.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of formula I," one to three compounds of formula I can be administered at the same time, preferably one.

As used herein, the term "composition" is intended to encompass a product comprising the specified ingredients in the specified amounts, as well as any product which results, directly or indirectly, from combination of the specified ingredients in the specified amounts.

The wavy line ∼∼∼ as a bond generally indicates a mixture of, or either of, the possible isomers, e.g., containing (R)- and (S)-stereochemistry. For example,

means containing both

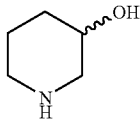

Lines drawn into the ring systems, such as, for example:

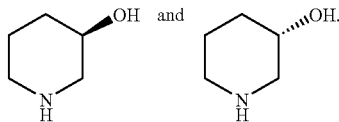

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

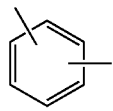

represents

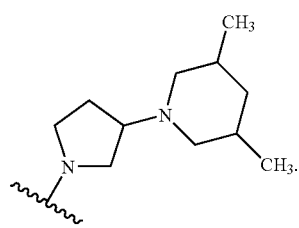

It should also be noted that any heteroatom with unsatisfied valences in the text, schemes, examples, structural formulae, and any Tables herein is assumed to have the hydrogen atom or atoms to satisfy the valences.

Those skilled in the art will recognize that certain compounds of formula I are tautomeric, and all such tautomeric forms are contemplated herein as part of the present invention.

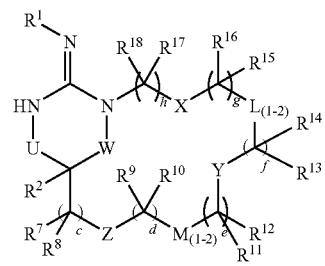

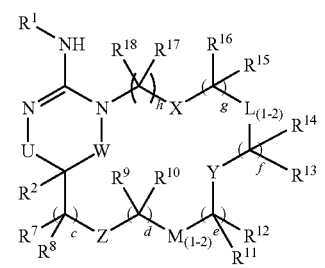

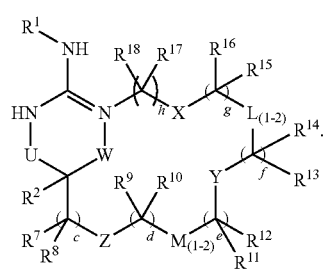

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate, ester or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate, ester or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-(C1-C2)alkyl and piperidino-, pyrrolidino- or morpholino($C_2$-$C_3$)alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl, —$C(OH)C(O)OY^1$ wherein $Y^1$ is H, ($C_1$-$C_6$)alkyl or benzyl, —$C(OY^2)Y^3$ wherein $Y^2$ is ($C_1$-$C_4$) alkyl and $Y^3$ is ($C_1$-$C_6$)alkyl, carboxy($C_1$-$C_6$)alkyl, amino ($C_1$-$C_4$)alkyl or mono-N- or di-N,N-($C_1$-$C_6$)alkylaminoalkyl, —$C(Y^4)Y^5$ wherein $Y^4$ is H or methyl and $Y^5$ is mono-N— or di-N,N-($C_1$-$C_6$)alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting aspartyl protease and/or inhibiting BACE-1 and thus producing the desired therapeutic effect in a suitable patient.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, bisulfates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered-equivalent to the free forms of the corresponding compounds for purposes of the invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "prodrug" and the like, is intended to equally apply to the salt, solvate and prodrug of enantiomers, stereoisomers, rotamers, tautomers, racemates or prodrugs of the inventive compounds.

Polymorphic forms of the compounds of formula I, and of the salts, solvates and prodrugs of the compounds of formula I, are intended to be included in the present invention Compounds of formula I can be made using procedures known in the art. The following reaction schemes show typical procedures, but those skilled in the art will recognize that other procedures can also be suitable.

In the Schemes and in the Example below, the following abbreviations are used:
high pressure liquid chromatography: HPLC
reverse-phase HPLC: RP-HPLC
liquid chromatography mass spectrometry: LCMS
mass spectrometry: MS
polytetrafluoroethylene: PTFE
hour: h
minute: min
retention time: $t_R$
ethyl: Et
methyl: Me
benzyl: Bn
lithium diisopropylamide: LDA
1-(3-dimethylaminopropyl)-3-ethyl carbodiimide hydrochloride: EDCl
DIEA means N,N-diisopropylethylamine
ethyl acetate: EtOAc
N,N-dimethylformamide: DMF
methanol: MeOH
Ethanol: EtOH
acetonitrile: $CH_3CN$
acetic acid: AcOH
magnesium sulfate: $MgSO_4$
copper iodide: CuI
diisopropylamine: $^iPr_2NH$
Dichlorobis(triphenylphosphine)palladium: $PdCl_2(PPh_3)_2$
ammonium hydroxide: $NH_4OH$
trifluoroacetic acid: TFA
benzyloxycarbonyl: Cbz
tert-butoxycarbonyl: Boc In Schemes 1 to 3, the variable "$R^x$" is used in place of variables $R^7$-$R^{18}$ in order to simplify the structures. "PG" refers to an amine protecting group. Examples of suitable amine protecting groups are Boc and Cbz, as well as Bn for secondary amines.

In Schemes 2 to 5, the curved line,

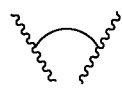

represents a chain of substituted or unsubstituted carbons or heteroatoms numbering 4 to 8.

In Scheme 1, an appropriately substituted bromophenyl ketone II can be converted into the corresponding hydantoin III under Bucherer-Bergs conditions. Base-mediated alkylation with suitable benzyl bromides or Mitsunobu-coupling with appropriate benzyl alcohols can provide access to derivative IV.

Coupling of aryl bromide IV with appropriately functionalized reagents in palladium-mediated Heck-, Suzuki-, Stille or Sonogashira-type reactions can afford an intermediate that can be converted into cyclization precursor V via reduction with hydrogen over palladium. V can be subjected to a sequence of amine deprotection and cyclization onto the ester or acid (examples of suitable R-groups in $CO_2R$ are H, Me, Et) to afford macrocyclic hydantoin VI. Conversion of the imide carbonyl group of VI with Lawesson's reagent can provide thiohydantoin VII, which can be subsequently subjected to oxidative amination conditions to afford desired iminohydantoin VIII.

Scheme 1:

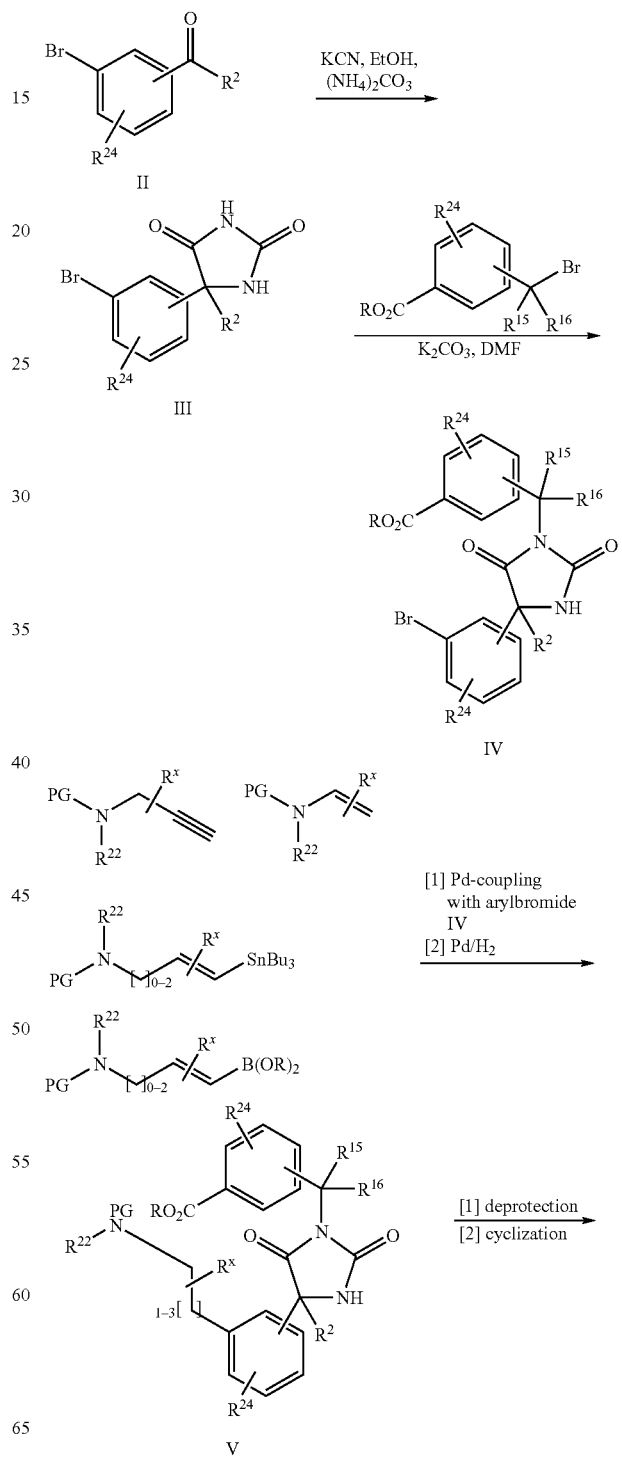

-continued

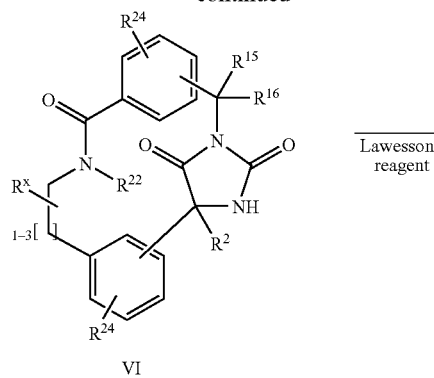

VI

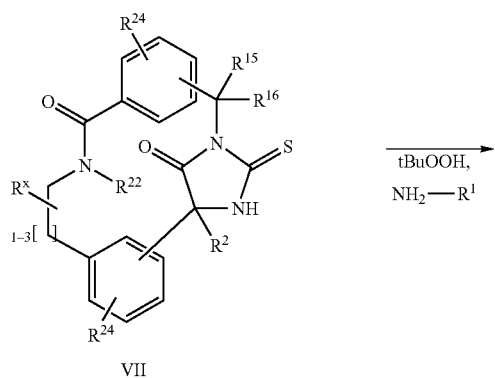

VII

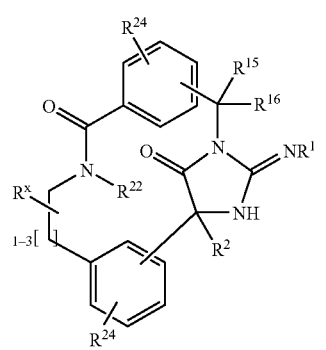

VIII

Scheme 2:

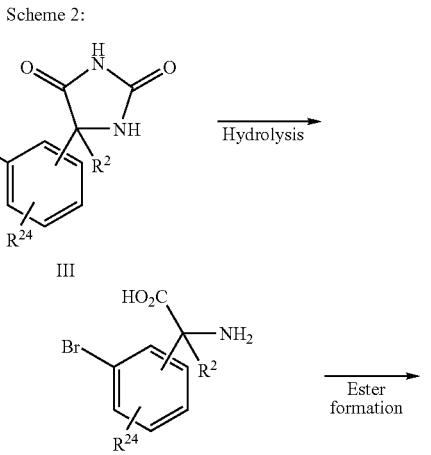

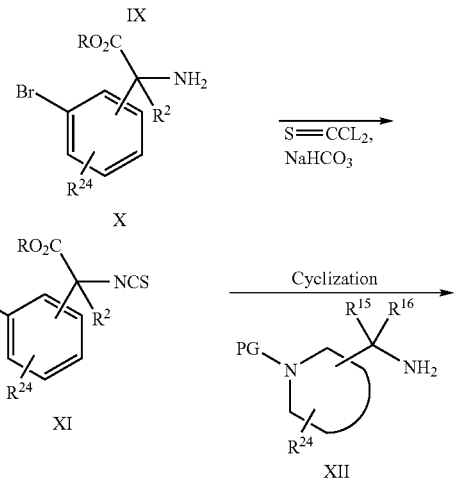

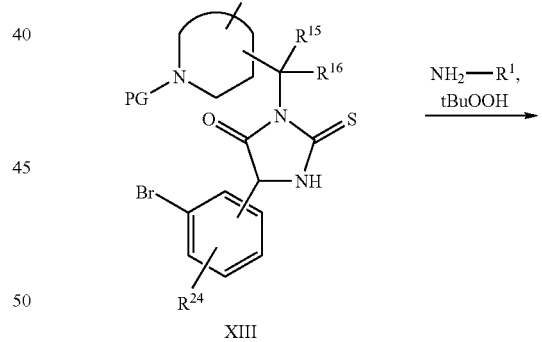

XIII

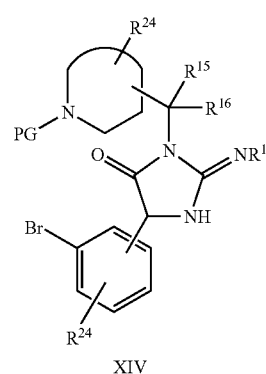

XIV

In Scheme 2, hydantoin III can be hydrolyzed under basic conditions to amino acid IX, which can be subsequently converted into ester X under conditions such as MeOH/HCl or TMS-diazomethane/MeOH. Thioisocyanate formation with thiophosgene delivers isothiocyanate XI, which can be reacted with an appropriately functionalized amine XII to afford thiohydantoin XIII. Oxidative amination with an amine/tert-BuOOH can afford iminohydantoin XIV.

In Scheme 3, coupling of aryl bromide XIV with appropriately functionalized reagents in palladium-mediated Heck-, Suzuki-, Stille or Sonogashira-type reactions can afford an intermediate that can be converted into cyclization precursor XV via reduction with hydrogen over palladium. XV can be subjected to a sequence of amine deprotection and cyclization onto the ester or acid (examples of suitable R-groups in CO$_2$R are H, Me, Et) to afford macrocyclic hydantoin XVI.

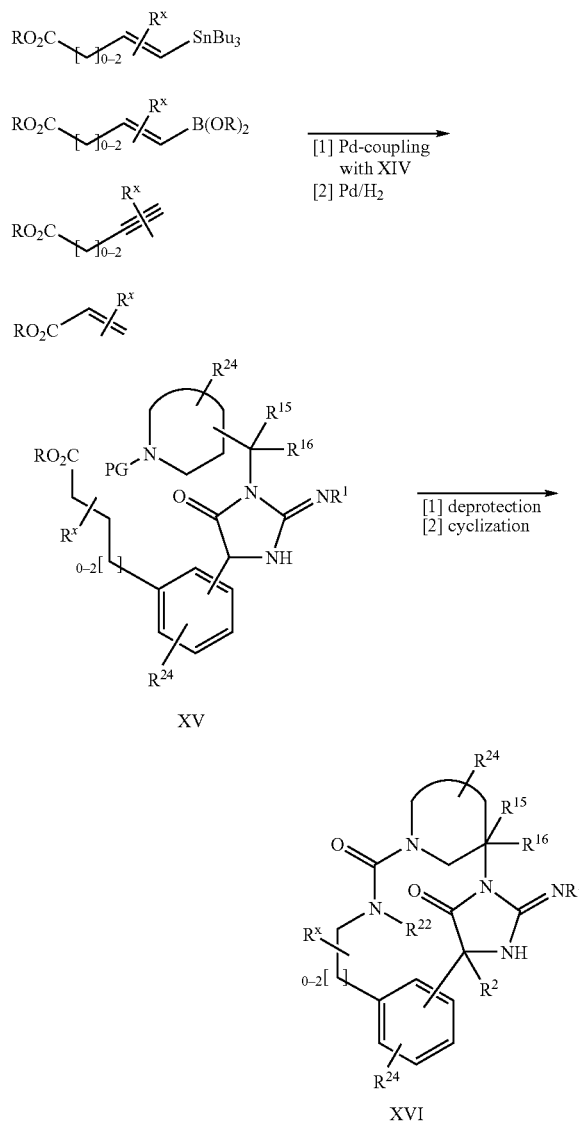

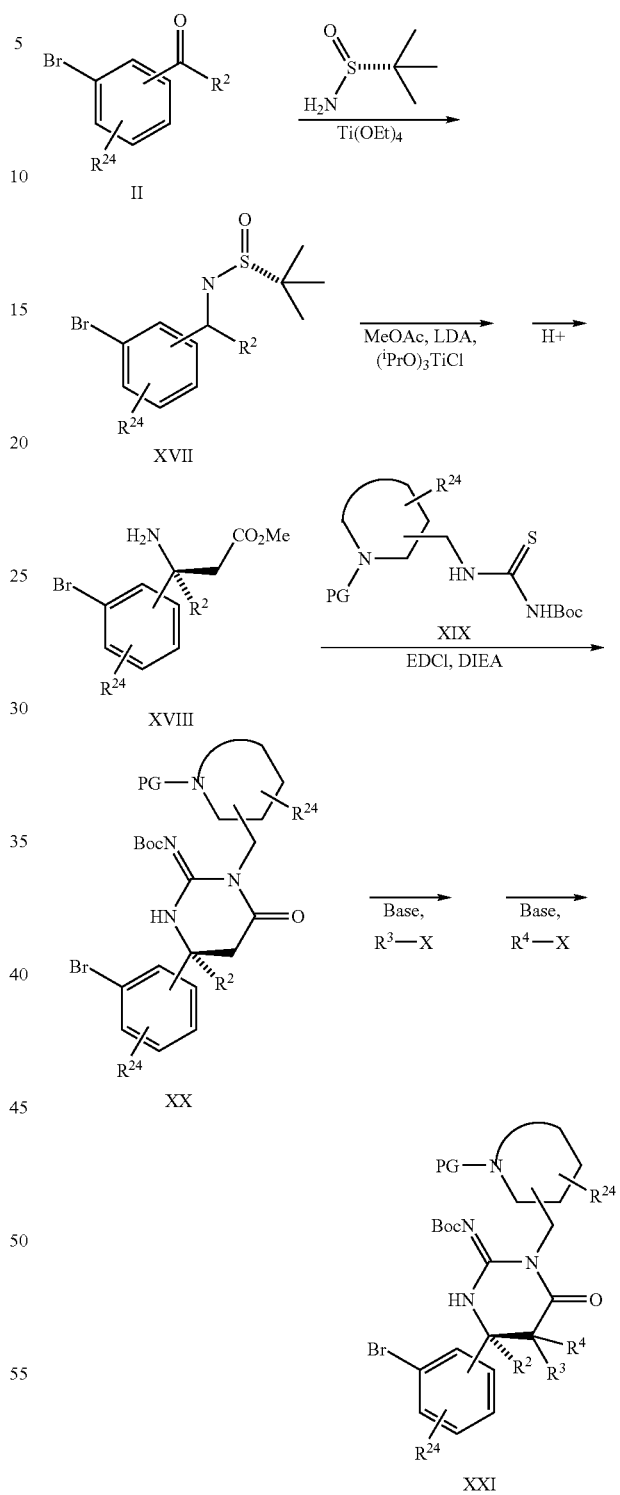

In Scheme 4, an appropriately substituted bromophenyl ketone II can be condensed with tert-butylsulfinamide, promoted by Lewis-acids such as Ti(OEt)$_4$. The resulting imine XVII can be treated with an ester enolate, and the adduct can be hydrolyzed under acidic conditions to give amino methylester XVIII. Coupling with thiourea XIX can afford iminopyrimidone XX, which can be alkylated with suitable electrophiles such as R$^3$X and R$^4$X to give intermediate XXI.

In Scheme 5, coupling of aryl bromide XXI with appropriately functionalized reagents in palladium-mediated Heck-, Suzuki-, Stille or Sonogashira-type reactions can afford an intermediate that can be converted into a cyclization precursor XXII via reduction with hydrogen over palladium. XXII can be subjected to a sequence of amine deprotection and cyclization onto the ester or acid (examples of suitable R-groups in CO₂R are H, Me, Et) to eventually afford macrocyclic iminopyrimidinone XXIII after removal of the imino-protecting group.

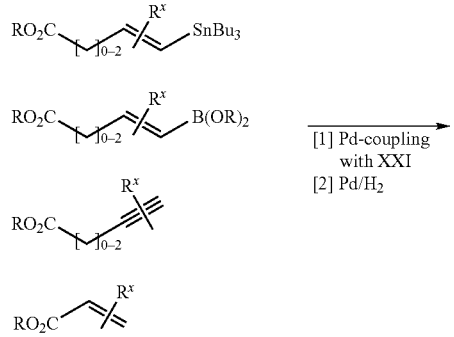

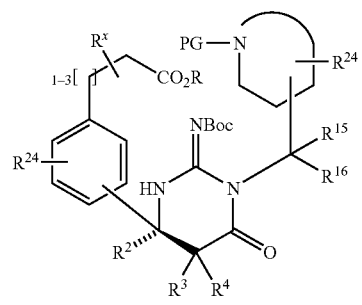

EXAMPLE 1

Synthesis of Macrocycle 7

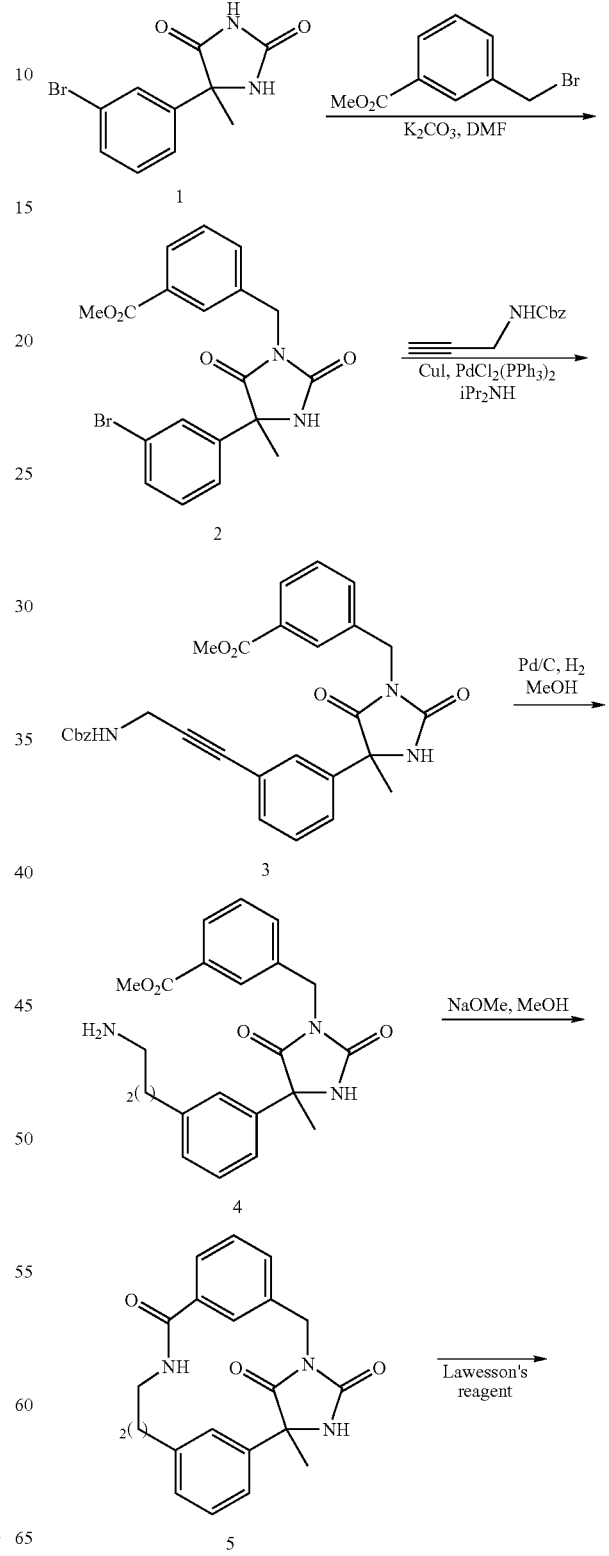

The conditions for the RP-HPLC and LCMS analysis in the preparation and example below can be as follows:

Conditions A: 5 minute gradient from 10%→95% CH₃CN/ H₂O with 0.1% TFA, then 2 min isocratic at 95% CH₃CN/ H₂O with 0.1% TFA, 1.0 mL/min flow rate on an analytical C18 reverse-phase column.

Conditions B: gradient from 10%→95% CH₃CN/H₂O with 0.1% HCO₂H, 30 mL/min flow rate on a preparative C18 reverse-phase column.

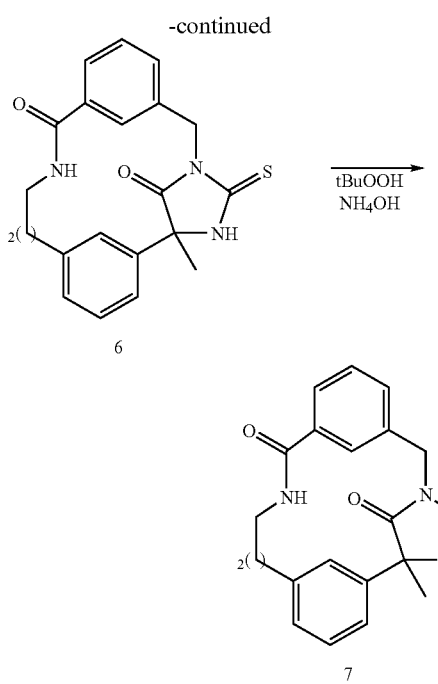

5-(3-Bromo-phenyl)-5-methyl-imidazolidine-2,4-dione (1): To a suspension of ammonium carbonate (20.5 g, 225 mmol) and potassium cyanide (8.6 g, 125 mmol) in EtOH/water (160 mL, 1/1) at 23° C. was added 3-bromoacetophenone (6.61 mL, 50 mmol). The pressure-tube was sealed and heated for 24 h at 95° C., then cooled to 23° C. The solution was diluted with water (300 mL), the solid removed by filtration and dried under vacuum to give the desired material (11.3 g, 84%). MS (ES+): 269/271 (M+H), 310/312 (M+H+CH$_3$CN).

3-[4-(3-Bromo-phenyl)-4-methyl-2,5-dioxo-imidazolidin-1-ylmethyl]-benzoic acid methyl ester (2): In analogy to the literature (Moloney et al., *J. Med. Chem.* 1997, 40, 2347-2362), methyl 3-bromomethylbenzoate (4.75 g, 20.7 mmol) was added to a suspension of hydantoin 1 (5.0 g, 18.6 mmol) and potassium carbonate (3.1 g, 22.5 mmol) in DMF (75 mL) at 23° C. After 18 h, the reaction mixture was partitioned between water and EtOAc, and the aqueous layer extracted with EtOAc. The combined organic layers were washed with water (1×), NaHCO$_3$ (1×), water (1×), brine (1×), then dried over MgSO$_4$. After filtration, concentration in vacuo gave an oil, which was subjected to silica gel chromatography (20→50% EtOAc/hexanes) to yield the desired material as a white sticky foam (8.32 g, 100%). $^1$H NMR (400 MHz, CDCl$_3$) δ 7.92 (m, 2H), 7.58 (m, 1H), 7.34-7.46 (m, 4H), 7.20 (m, 2H), 4.66 (s, 2H), 3.84 (s, 3H), 1.76 (s, 3H).

3-(4-[3-(3-Benzyloxycarbonylamino-prop-1-ynyl)-phenyl]-4-methyl-2,5-dioxo-imidazolidin-1-ylmethyl)-benzoic acid methyl ester (3): A mixture of hydantoin 2 (830 mg, 2 mmol), N-Cbz-propargylamine (460 mg, 2.43 mmol; prepared according to the literature by Yasuda et al., patent application 2003, US 2003/0004353), CuI (20 mg, 0.1 mol), PdCl$_2$(PPh$_3$)$_2$ (70 mg, 0.1 mmol) and iPr$_2$NH (850 μL, 6 mmol) in DMF (5 mL) was heated for 15 min at 100° C. (Smith Microwave Synthesizer). The reaction mixture was diluted with EtOAc, washed with 1 M HCl (2×), NaHCO$_3$ (1×), water (3×) and brine (1×), then dried over MgSO$_4$, filtered and concentrated under vacuum. The crude material was subjected to silica gel chromatography (30→50% EtOAc/hexanes) to yield the desired material as a colorless film (598 mg, 57%). $^1$H NMR (400 MHz, CDCl$_3$) δ 7.89 (m, 2H), 7.21-7.46 (m, 12H), 6.71 (bs, 1H), 4.62 (s, 2H), 4.12 (m, 2H), 3.81 (s, 3H), 1.72 (s, 3H). MS (ES+): 526 (M+H).

3-{4-[3-(3-Amino-propyl)-phenyl]-4-methyl-2,5-dioxo-imidazolidin-1-ylmethyl}-benzoic acid methyl ester (4): A solution of the Cbz-protected propargylamine 3 (580 mg, 1.1 mmol) and acetic acid (50 μL) in MeOH (10 mL) was stirred over 10% Pd/C (284 mg) under an atmosphere of hydrogen (50 psi) for 18 h. The suspension was passed through a PTFE-filter and the resulting filtrate concentrated under vacuum to give the desired material as a yellow solid (440 mg, 100%). $^1$H NMR (400 MHz, CDCl$_3$) δ 8.32 (bs, 1H), 8.05 (bs, 2H), 7.83-7.88 (m, 2H), 7.34-7.41 (m, 3H), 7.27 (m, 1H), 7.14 (m, 1H), 6.95 (m, 1H), 4.57 (s, 2H), 3.79 (s, 3H), 3.39 (m, 2H), 2.86 (m, 2H), 2.60 (m, 2H), 2.00 (m, 2H), 1.65 (s, 3H). MS (ES+): 396 (M+H), 418 (M+Na).

2-Methyl-3,5,13-triazatetracyclo[15.3.1.1(2,5).1(7,11)]tricosa-1(21),7,9,11(22),17,19-hexaene-4,12,23-trione (5): A solution of amino methylester 4 (120 mg, 300 μmol) in MeOH (40 mL) was heated in the presence of sodium methoxide (30 wt % solution in MeOH, 300 μL, 900 μmol) for 4 days at 85° C. The reaction mixture was cooled to 23° C., acidified with AcOH (50 μL) and concentrated in vacuo to give a solid that was subjected to RP-HPLC (conditions B) to give the desired macrocycle as a white solid (52 mg, 48%). $^1$H NMR (400 MHz, CD$_3$OD) δ 7.56 (m, 1H), 7.47-7.52 (m, 2H), 7.28-7.41 (m, 4H), 7.20 (m, 1H), 6.79 (bs, 1H), 4.71 (s, 2H), 3.25-3.44 (m, 2H), 2.90-2.97 (m, 1H), 2.60-2.67 (m, 1H), 2.12-2.17 (m, 1H), 1.96-2.03 (m, 1H), 1.80 (s, 3H). LCMS (Conditions A): $t_R$=2;78 min: 364.1 (M+H).

Thiohydantoin (6): A suspension of macrocyclic hydantoin 5 (50 mg, 137 μmol) and Lawesson's reagent (66 mg, 165 μmol) in toluene (2 mL) was heated for 18 h at 95° C. in a sealed vial. After cooling the reaction to 23° C., the suspension was partitioned between EtOAc and NaHCO$_3$. The aqueous phase was extracted with EtOAc (1×), and the combined organic layers washed with NaHCO$_3$ (2×), water (1×) and brine (1×), then dried over MgSO$_4$, filtered and concentrated under vacuum. The crude material was subjected to RP-HPLC (conditions B) to give the desired macrocyclic thiohydantoin 6 (36 mg, 70%) along with dithiohydantoin (7 mg, 13%). $^1$H NMR (400 MHz, CD$_3$OD) δ 7.65-7.78 (m, 3H), 7.44 (m, 1H), 7.22-7.40 (m, 2H), 6.81-6.95 (m, 3H), 6.57 (m, 1H), 4.71 (m, 2H), 3.80 (m, 2H), 2.91 (m, 1H), 2.69 (m, 1H), 2.34 (m, 1H), 2.19 (m, 1H), 1.81 (m, 3H). MS (ES+): 380 (M+H).

4-Imino-2-methyl-3,5,13-triazatetracyclo[15.3.1.1(2,5).1(7,11)]tricosa-1(21),7,9,11(22),17,19-hexaene-12,23-dione (7): To a suspension of macrocyclic thiohydantoin 6 (36 mg, 95 μmol) in MeOH (4 mL) at 23° C. was added concentrated NH$_4$OH solution (28% in water, 1 mL) and tert-butylhydrogenperoxide (70% in water, 1 mL). The reaction was stirred for 2 days at 23° C., then concentrated under vacuum. The residue was suspended in MeOH (2 mL), passed through a PTFE-filter and the filtrate subjected to RP-HPLC (conditions B) to give the desired material. The formate salt resulting from the reverse-phase HPLC was treated with 1 M HCl/MeOH for 15 min at 23° C., then concentrated to give the HCl-salt of macrocyclic iminohydantoin 7 as a colorless film (15.9 mg, 42%). $^1$H NMR (400 MHz, CD$_3$OD) revealed the presence of rotamers. LCMS (Conditions A): $t_R$=2.20 min: 363 (M+H—HCl).

Human Cathepsin D FRET Assay

The substrate used below has been described (Y. Yasuda et al., J. Biochem., 125, 1137 (1999)). Substrate and enzyme are commercially available.

The assay can be run in a 30 μl final volume using a 384 well Nunc black plate. 8 concentrations of compound can be pre-incubated with enzyme for 30 mins at 37° C. followed by addition of substrate with continued incubation at 37° C. for 45 mins. The rate of increase in fluorescence is linear for over 1 h and is measured at the end of the incubation period using a Molecular Devices FLEX station plate reader. Kis are interpolated from the IC50s using a Km value of 4 μM and the substrate concentration of 2.5 μM.

Reagents
Na-Acetate pH 5
1% Brij-35 from 10% stock (Calbiochem)
DMSO
Purified (>95%) human liver Cathepsin D (Athens Research & Technology Cat# 16-12-030104)
Peptide substrate (Km=4 uM) Mca-Gly-Lys-Pro-Ile-Leu-Phe-Phe-Arg-Leu-Lys(Dnp)-D-Arg-NH$_2$ Bachem Cat # M-2455
Pepstatin is used as a control inhibitor (Ki~0.5 nM) and is available from Sigma.
Nunc 384 well black plates Final Assay Buffer Conditions
100 mM Na Acetate pH 5.0
0.02% Brij-35
1% DMSO Compound can be diluted to 3× final concentration in assay buffer containing 3% DMSO. 10 μl of compound will be added to 10 μl of 2.25 nM enzyme (3×) diluted in assay buffer without DMSO, mixed briefly, spun, and can be incubated at 37° C. for 30 mins. 3× substrate (7.5 μM) is prepared in 1× assay buffer without DMSO. 10 μl of substrate will be added to each well mixed and spun briefly to initiate the reaction. Assay plates can be incubated at 37 C for 45 mins and read on 384 compatible fluorescence plate reader using a 328 nm Ex and 393 nm Em.

BACE-1 Cloning, Protein Expression and Purification

A predicted soluble form of human BACE1 (sBACE1, corresponding to amino acids 1-454) can be generated from the full length BACE1 cDNA (full length human BACE1 cDNA in pcDNA4/mycHisA construct; University of Toronto) by PCR using the advantage-GC cDNA PCR kit (Clontech, Palo Alto, Calif.). A HindIII/PmeI fragment from pcDNA4-sBACE1myc/His can be blunt ended using Klenow and subcloned into the Stu I site of pFASTBACI(A) (Invitrogen). A sBACE1mycHis recombinant bacmid can be generated by transposition in DH10Bac cells (GIBCO/BRL). Subsequently, the sBACE1 mycHis bacmid construct can be transfected into sf9 cells using CellFectin (Invitrogen, San Diego, Calif.) in order to generate recombinant baculovirus. Sf9 cells are grown in SF 900-II medium (Invitrogen) supplemented with 3% heat inactivated FBS and 0.5× penicillin/streptomycin solution (Invitrogen). Five milliliters of high titer plaque purified sBACEmyc/His virus is used to infect 1 L of logarithmically growing sf9 cells for 72 hours. Intact cells are pelleted by centrifugation at 3000×g for 15 minutes. The supernatant, containing secreted sBACE1, is collected and diluted 50% v/v with 100 mM HEPES, pH 8.0. The diluted medium is loaded onto a Q-sepharose column. The Q-sepharose column is washed with Buffer A (20 mM HEPES, pH 8.0, 50 mM NaCl).

Proteins, can be eluted from the Q-sepharose column with Buffer B (20 mM HEPES, pH 8.0, 500 mM NaCl). The protein peaks from the Q-sepharose column are pooled and loaded onto a Ni-NTA agarose column. The Ni-NTA column can be then washed with Buffer C (20 mM HEPES, pH 8.0, 500 mM NaCl). Bound proteins are then eluted with Buffer D (Buffer C+250 mM imidazole). Peak protein fractions as determined by the Bradford Assay (Biorad, CA) are concentrated using a Centricon 30 concentrator (Millipore). sBACE1 purity is estimated to be ~90% as assessed by SDS-PAGE and Commassie Blue staining. N-terminal sequencing indicates that greater than 90% of the purified sBACE1 contained the prodomain; hence this protein is referred to as sproBACE1.

Peptide Hydrolysis Assay

The inhibitor, 25 nM EuK-biotin labeled APPsw substrate (EuK-KTEEISEVNLDAEFRHDKC-biotin; CIS-Bio International, France), 5 μM unlabeled APPsw peptide (KTEEISEVNLDAEFRHDK; American Peptide Company, Sunnyvale, Calif.), 7 nM sproBACE1, 20 mM PIPES pH 5.0, 0.1% Brij-35 (protein grade, Calbiochem, San Diego, Calif.), and 10% glycerol are preincubated for 30 min at 30° C. Reactions are initiated by addition of substrate in a 5 μl aliquot resulting in a total volume of 25 μl. After 3 hr at 30° C. reactions are terminated by addition of an equal volume of 2× stop buffer containing 50 mM Tris-HCl pH 8.0, 0.5 M KF, 0.001% Brij-35, 20 μg/ml SA-XL665 (cross-linked allophycocyanin protein coupled to streptavidin; CIS-Bio International, France) (0.5 μg/well). Plates are shaken briefly and spun at 1200×g for 10 seconds to pellet all liquid to the bottom of the plate before the incubation. HTRF measurements are made on a Packard Discovery® HTRF plate reader using 337 nm laser light to excite the sample followed by a 50 μs delay and simultaneous measurements of both 620 nm and 665 nm emissions for 400 μs.

$IC_{50}$ determinations for inhibitors, (I), are determined by measuring the percent change of the relative fluorescence at 665 nm divided by the relative fluorescence at 620 nm, (665/620 ratio), in the presence of varying concentrations of I and a fixed concentration of enzyme and substrate. Nonlinear regression analysis of this data can be performed using GraphPad Prism 3.0 software selecting four parameter logistic equation, that allows for a variable slope. Y=Bottom+(Top−Bottom)/(1+10^((LogEC50−X)*Hill Slope)); X is the logarithm of concentration of 1, Y is the percent change in ratio and Y starts at bottom and goes to top with a sigmoid shape.

Human Mature Renin Enzyme Assay

Human Renin can be cloned from a human kidney cDNA library and C-terminally epitope-tagged with the V5-6His sequence into pcDNA3.1. pCNDA3.1-Renin-V5-6His is stably expressed in HEK293 cells and purified to >80% using standard Ni-Affinity chromatography. The prodomain of the recombinant human renin-V5-6His can be removed by limited proteolysis using immobilized TPCK-trypsin to give mature-human renin. Renin enzymatic activity can be monitored using a commercially available fluorescence resonance energy transfer (FRET) peptide substrate, RS-1 (Molecular Probes, Eugene, Oreg.) in 50 mM Tris-HCl pH 8.0, 100 mM NaCl, 0.1% Brij-35 and 5% DMSO buffer for 40 mins at 30° celsius in the presence or absence of different concentrations of test compounds. Mature human Renin is present at approximately 200 nM. Inhibitory activity is defined as the percent decrease in renin induced fluorescence at the end of the 40 min incubation compared to vehicle controls and samples lacking enzyme.

In the aspect of the invention relating to a combination of at least one compound of formula I with at least one cholinesterase inhibitor, acetyl- and/or butyrylcholinesterase inhibitors can be used. Examples of cholinesterase inhibitors are tacrine, donepezil, rivastigmine, galantamine, pyridostigmine and neostigmine, with tacrine, donepezil, rivastigmine and galantamine being preferred. Preferably, these combinations are directed to the treatment of Alzheimer's Disease.

In one aspect of the invention, a combination of at least one compound of formula I with at least one muscarinic $m_1$ agonist or $m_2$ antagonist can be used. Examples of $m_1$ agonists are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

In other aspects of the invention relating to a combination of at least one compound of formula I and at least one other agent, for example a beta secretase inhibitor; a gamma secretase inhibitor; an HMG-CoA reductase inhibitor such as atorvastatin, lovastatin, simvastatin, pravastatin, fluvastatin and rosuvastatin; non-steroidal anti-inflammatory agents such as, but not necessarily limited to ibuprofen, relafen or naproxen; N-methyl-D-aspartate receptor antagonists such as memantine; anti-amyloid antibodies including humanized monoclonal antibodies; vitamin E; nicotinic acetylcholine receptor agonists; CB1 receptor inverse agonists or CB1 receptor antagonists; antibiotics such as doxycycline; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity. Preferably, these combinations are directed to the treatment of Alzheimer's Disease.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

When a compound of formula I is used in combination with a cholinesterase inhibitor to treat cognitive disorders, these two active components may be co-administered simultaneously or sequentially, or a single pharmaceutical composition comprising a compound of formula I and a cholinesterase inhibitor in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the cholinesterase inhibitor can be determined from published material, and may range from 0.001 to 100 mg/kg body weight.

When separate pharmaceutical compositions of a compound of formula I and a cholinesterase inhibitor are to be administered, they can be provided in a kit comprising in a single package, one container comprising a compound of formula I in a pharmaceutically acceptable carrier, and a separate container comprising a cholinesterase inhibitor in a pharmaceutically acceptable carrier, with the compound of formula I and the cholinesterase inhibitor being present in amounts such that the combination is therapeutically effective. A kit is advantageous for administering a combination when, for example, the components must be administered at different time intervals or when they are in different dosage forms.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We Claim:
1. A compound having the structural formula

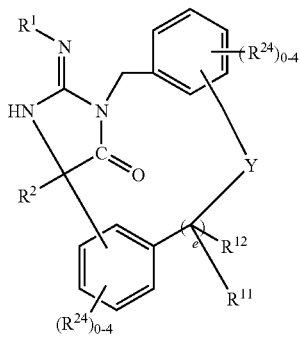

or a pharmaceutically acceptable salt or ester thereof, wherein
$R^1$ is selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, —$OR^{19}$, —CN, —C(O)$R^{20}$, —C(O)O$R^{19}$, —S(O)$_{1-2}R^{21}$, —C(O)N($R^{22}$)($R^{23}$), —S(O)$_{1-2}$N($R^{22}$)($R^{23}$), —$NO_2$, —N═C($R^{22}$)($R^{23}$) and —N($R^{22}$)($R^{23}$);

$R^2$ is selected from the group consisting of H, alkyl, alkenyl, alkynyl, cycloalkyl, cycloalkylal kyl, heterocycloalkyl, heterocycloalkylalkyl, aryl, arylalkyl, heteroaryl, heteroarylalkyl, arylcycloalkyl, —$CF_3$, —CN, —C(O)$R^{20}$, —C(O)O$R^{19}$, and —C(O)N($R^{22}$)($R^{23}$);

e is 3;

$R^{11}$ and $R^{12}$ are each independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, halo, —$CF_3$ —SH, —$OR^{19}$, —CN, —C(O)$R^{20}$, —C(O)O$R^{19}$, —S(O)$_{0-2}R^{21}$, —S(O)$_{1-2}$N($R^{22}$)($R^{23}$), —C(O)N($R^{22}$)($R^{23}$), —N($R^{22}$)C(O)$R^{20}$, —N($R^{22}$)C(O)N($R^{22}$)($R^{23}$), —N($R^{22}$)C(O)O$R^{19}$, —N($R^{22}$)S(O)$_{1-2}R^{21}$, —$NO_2$, —N═C($R^{22}$)($R^{23}$) and —N($R^{22}$)($R^{23}$), Y is selected from the group consisting of —O—, —N($R^5$)—, —C(O)—, —S(O)$_{0-2}$—, —C(O)N($R^{22}$)—, —N($R^{22}$)C(O)—, —S(O)$_{1-2}$N($R^{22}$)—, —N($R^{22}$)S(O)$_{1-2}$— or a bond;

$R^{19}$ is H, alkyl, alkenyl, alkynyl, aryl, cycloalkyl, cycloalkylalkyl, heteroaryl, arylalkyl, heteroarylalkyl, heterocycloalkyl or heterocycloalkylalkyl;

$R^{20}$ is H, alkyl, alkenyl, alkynyl, aryl, cycloalkyl, cycloalkylalkyl, heteroaryl, arylalkyl, heteroarylalkyl, heterocycloalkyl, heterocycloalkylalkyl, —$NH_2$, —NH(alkyl), or —N(alkyl)$_2$;

$R^{21}$ is alkyl, alkenyl, alkynyl, aryl, cycloalkyl, cycloalkylalkyl, heteroaryl, arylalkyl, heteroarylalkyl, heterocycloalkyl or heterocycloalkylalkyl;

$R^{22}$ and $R^{23}$ are H, alkyl, alkenyl, alkynyl, aryl, cycloalkyl, cycloalkylalkyl, heteroaryl, arylalkyl, heteroarylalkyl, heterocycloalkyl or heterocycloalkylalkyl; and each $R^{24}$ is independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, halo, —$CF_3$, —SH, —$OR^{19}$, —CN, —C(O)$R^{20}$, —C(O)O$R^{19}$, —S(O)$_{0-2}R^{21}$, —S(O)$_{1-2}$N($R^{22}$)($R^{23}$), —C(O)N($R^{22}$)($R^{23}$), —N($R^{22}$)C(O)$R^{20}$, —N($R^{22}$)C(O)N($R^{22}$)($R^{23}$), —N($R^{22}$)C(O)O$R^{19}$, —N($R^{22}$)S(O)$_{1-2}R^{21}$, —$NO_2$, —N═C($R^{22}$)($R^{23}$) and —N($R^{22}$)($R^{23}$);

wherein s is 1 or 2 and t is 1 or 2.

2. A compound of claim 1, or a pharmaceutically acceptable salt or ester thereof, wherein Y is —C(O)N($R^{22}$)— or —N($R^{22}$)C(O)—.

3. A compound of claim 1 wherein Y is —C(O)N($R^{22}$)—.

4. A compound according to claim 1, or a pharmaceutically acceptable salt or ester thereof, with the following structure

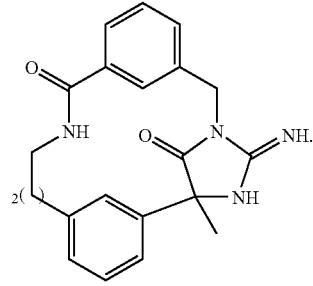

5. A pharmaceutical composition comprising an effective amount of a compound of claim 1, or a pharmaceutically acceptable salt or ester thereof, and a pharmaceutically effective carrier.

6. A pharmaceutical composition comprising an effective amount of a compound of claim 1, and an effective amount of a cholinesterase inhibitor or a muscarinic $m_1$ agonist or $m_2$ antagonist, in a pharmaceutically effective carrier.

7. A pharmaceutical composition comprising an effective amount of a compound of claim 1, and an effective amount of a gamma secretase inhibitor; an HMG-CoA reductase inhibitor or a non-steroidal anti-inflammatory agent.

8. A pharmaceutical composition comprising an effective amount of a compound of claim 4, or a pharmaceutically acceptable salt or ester thereof, and a pharmaceutically effective carrier.

9. A compound of claim 1, wherein $R^1$ is selected from the group consisting of H and alkyl.

10. A compound of claim 1, wherein $R^1$ is H.

11. A compound of claim 1, wherein $R^2$ is selected from the group consisting of H, alkyl, cycloalkyl, cycloalkylalkyl, aryl, arylalkyl, heteroaryl, heteroarylalkyl, —$CF_3$, —CN, —C(O)$R^{20}$, —C(O)O$R^{19}$, and —C(O)N($R^{22}$)($R^{23}$).

12. A compound of claim 1, wherein $R^2$ is selected from the group consisting of H, alkyl, phenyl, benzyl, —C(O)OH, —C(O)Oalkyl, —C(O)Ophenyl, —C(O)alkyl, —C(O)NH-phenyl, —C(O)NH-pyridyl, —C(O)NH-thiophenyl, OH, —O-alkyl, and —O-cycloalkyl.

* * * * *